United States Patent [19]

Tosa et al.

[11] Patent Number: 5,578,455
[45] Date of Patent: Nov. 26, 1996

[54] METHOD FOR DETERMINING ENDOTOXIN AND APPARATUS THEREFOR

[75] Inventors: Tetsuya Tosa, Kyoto; Takeji Shibatani, Kobe; Taizo Watanabe, Nagaokakyo; Satoshi Minobe, Otsu; Makoto Masuda, Takarazuka, all of Japan

[73] Assignee: Tanabe Seiyaku Co., Ltd., Osaka, Japan

[21] Appl. No.: 209,247

[22] Filed: Mar. 14, 1994

[30] Foreign Application Priority Data

Mar. 19, 1993 [JP] Japan .................................. 5-060569

[51] Int. Cl.⁶ ........................ G01N 33/569; G01N 33/579
[52] U.S. Cl. ......................... 435/7.32; 422/58; 422/59; 422/101; 435/7.37; 435/287.1; 435/287.2; 435/287.3; 435/288.1; 435/288.6; 436/161; 436/501; 436/807; 436/810; 530/412; 530/413; 530/415; 210/656; 210/660; 210/662
[58] Field of Search .................................. 210/656, 660, 210/662; 422/58, 59, 101; 435/7.32, 7.37, 287.1, 287.2, 287.3, 288.1, 288.6; 436/161, 501, 807, 810; 530/412, 413, 415

[56] References Cited

U.S. PATENT DOCUMENTS

| | | | |
|---|---|---|---|
| 3,897,309 | 7/1975 | Grabner | 195/66 |
| 3,944,391 | 3/1976 | Harris et al. | 210/24 |
| 3,959,128 | 5/1976 | Harris | 424/101 |
| 4,059,512 | 11/1977 | Harris | 210/24 |
| 4,276,050 | 6/1981 | Firca et al. | 435/4 |
| 5,186,839 | 2/1993 | Kimura et al. | 210/656 |
| 5,336,412 | 8/1994 | Huse et al. | 210/635 |
| 5,342,785 | 8/1994 | Tosa et al. | 436/178 |

FOREIGN PATENT DOCUMENTS

| | | |
|---|---|---|
| 0121868A1 | 10/1984 | European Pat. Off. . |
| 0350004 | 1/1990 | European Pat. Off. . |
| 0456252 | 11/1991 | European Pat. Off. . |
| 3149117A1 | 6/1983 | Germany . |
| 2077429 | 12/1981 | United Kingdom . |

*Primary Examiner*—James C. Housel
*Assistant Examiner*—Christopher L. Chin
*Attorney, Agent, or Firm*—Browdy and Neimark

[57] ABSTRACT

There is disclosed a method for determining an endotoxin by reacting the endotoxin adsorbed on an adsorbent having specific endotoxin adsorbability with an endotoxin detecting reagent, including the steps of:

(a) preparing a column having a tip opening, a rear end opening and an adsorbent-filling and holding means provided in the column through which a sample solution can pass, (b) introducing the endotoxin adsorbent into the column through the tip opening to fill and hold the adsorbent therein, (c) introducing the sample solution into the column through the tip opening and discharging the introduced sample solution through the rear end opening to contact the sample and the adsorbent and thereby adsorbing the endotoxin on the adsorbent, and (d) reacting the detecting reagent with the endotoxin adsorbed on the adsorbent.

There is also disclosed an apparatus for the above method.

13 Claims, 2 Drawing Sheets

METHOD FOR DETERMINING ENDOTOXIN AND APPARATUS THEREFOR

BACKGROUND OF THE INVENTION

The present invention relates to an improved method for determining an endotoxin and an apparatus therefor.

An endotoxin, one kind of pyrogen, has been measured by a fever test using rabbits. However, the fever test using rabbits is being replaced by a test utilizing Limulus Amebocyte Lysate (LAL), derived from circulating blood cells of horseshoe crab, *Limulus polyphemus,* (Limulus test). Since a Limulus reaction is inhibited or promoted by substances present in a measurement system, a certain pre-treatment to remove the influence of substances must be done in many cases. Examples of pre-treatment include dilution, heating, perchloric acid treatment and the like. However, all of these pre-treatments are insufficient to provide endotoxin measurement in having acceptable specificity, sensitivity and quantitativeness. In order to solve these problems, the present inventors have already developed a method for determining an endotoxin using an endotoxin adsorbent (EP-A 350004).

In order to improve the operation properties of the above method, the present inventors have also proposed another method wherein an endotoxin is adsorbed on an adsorbent and a reaction of adsorbed endotoxin with a Limulus reagent is carried out in a centrifugal filtration apparatus (EP-A 456252).

OBJECTS OF THE INVENTION

In the above methods, there still remain problems to be resolved in respect of operations in order to carry out the measurement at higher precision. That is, close attention must be paid to prevent contamination by endotoxins or reaction inhibiting substances derived from the outer atmosphere during operations. In addition, operations are not necessarily easily automated so that a large number of samples are treated more simply in a shorter period of time.

Therefore, a main object of the present invention is to provide a further improved method for determining an endotoxin which is easy to operate and automate and an apparatus therefor.

This object as well as other objects and advantages of the present invention will become apparent to those skilled in the art from the following description with reference to the accompanying drawings.

SUMMARY OF THE INVENTION

Figure 1:
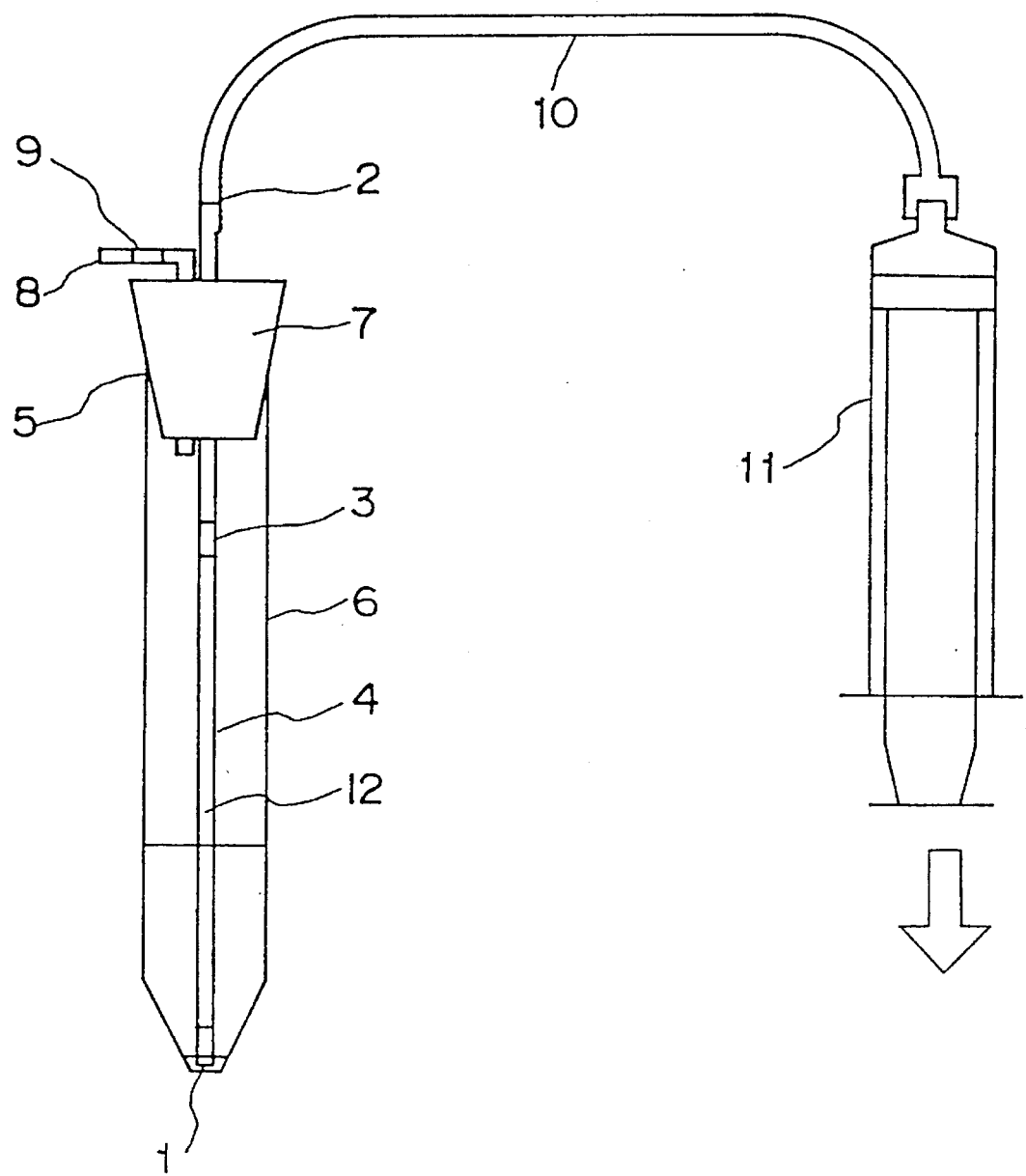
FIG. 1 is a schematic view illustrating one embodiment of the apparatus for determination of the present invention.

The present invention provides a method for determining an endotoxin by reacting the endotoxin adsorbed on an adsorbent having specific endotoxin adsorbability with an endotoxin detecting reagent, which comprises the steps of:

(a) preparing a column having a tip opening, a rear end opening and an adsorbent-filling and holding means provided in the column through which a sample solution can pass, (b) introducing the endotoxin adsorbent into the column through the tip opening to fill and hold the adsorbent therein, (c) introducing the sample solution into the column through the tip opening and discharging the introduced sample solution through the rear end opening to contact the sample and the adsorbent and thereby adsorbing the endotoxin on the adsorbent, and (d) reacting the detecting reagent with the endotoxin adsorbed on the adsorbent.

The step (d) in this method can be carried out usually by discharging the adsorbent having the endotoxin adsorbed thereon into the detecting reagent through the tip opening of the column, or introducing the detecting reagent into the column through the tip opening of the column. When the step (d) is carried out by introducing the detecting reagent into the column, after introduction of the reagent, the adsorbent and the detecting reagent may be discharged through the tip opening from the column.

The present invention also provides an apparatus for determining an endotoxin by reacting an endotoxin adsorbed on the adsorbent having specific endotoxin adsorbability with an endotoxin detecting reagent, which comprises:

a column having a tip opening, a rear end opening and an adsorbent-filling and holding means provided in the column through which a sample solution can pass, at least one container having one opened end which can contain therein an adsorbent suspension, and a sample solution or a detecting reagent, the tip part of the column being able to be inserted into the container, a means for maintaining the column in the contained state in the container, and a negative pressure loading means communicated with a rear end of the column.

DETAILED DESCRIPTION OF THE INVENTION

As the adsorbent having specific endotoxin adsorbability to be used in the present invention, any adsorbents can be used, in so far as they specifically adsorb thereon an endotoxin and the adsorbed endotoxin dose not lose its reactivity with the endotoxin detecting reagent. For example, adsorbents disclosed in EP-A 350004 by the present inventors can be used. Among them, adsorbents comprising a water-insoluble carrier such as cellulose, agarose and the like having nitrogen-containing heterocyclic compound bound thereto via a spacer such as alkylenediamine and the like are appropriately used. Such the heterocyclic compounds are selected from the group consisting of histidine, histamine and adenine. The shape of the adsorbent is preferably in the form of beads in view of easy filling in the column, minimizing pressure loss and the like. The adsorbents are commercially available and, for example, PYROSEP absorbent beads (trade name, manufactured by TANABE SEIYAKU CO., LTD.) and the like can be suitably used.

The method of the present invention comprises the steps of: preparing a column having a tip opening, a rear end opening and an adsorbent-filling and holding means provided in the column through which a sample solution can pass and the above steps (b) to (d); that is, filling the endotoxin adsorbent in the column, introducing the sample solution in the column and adsorbing an endotoxin on the endotoxin adsorbent, reacting the adsorbed endotoxin with a detecting reagent and detecting and determining the endotoxin and, if necessary, discharging the reaction solution from the column and incubating the reaction solution to carry out detection and measurement of an endotoxin. In addition, the above filling and adsorption steps may be carried out in one step by contacting the adsorbent and the sample solution and then filling them in the column.

Examples of the means for holding the filled endotoxin adsorbent which is provided in the column include a filter, such as glass filter, through which the sample solution can pass, while the adsorbent does not.

Thus, the method of the present invention is carried out as follows. For filling the endotoxin adsorbent in the column and holding it therein, a suspension of the endotoxin adsorbent is firstly introduced in the column through the tip opening thereof. The suspension is not limited to specific one. A suspension containing 1 to 50 wt % adsorbent in endotoxin-free water can usually be used.

Generally, the negative pressure is applied to the rear end opening of the column to introduce the suspension of the endotoxin adsorbent in the column to fill it in the column. The negative pressure can be applied by suction using a plunger such as injection cylinder, vacuum pump, tube pump and the like. In view of easy uniform filling and holding, the column is preferably maintained in the perpendicular direction.

Then, the negative pressure is further increased to introduce the aliquots of sample solution into the column through the tip opening. A sample to be measured is in the form of liquid such as solution, for example, a solution containing water, preferably, aqueous solution.

The sample solution is passed through a layer filled with the endotoxin adsorbent and is discharged through the rear end opening of the column by suction using the negative pressure, during which an endotoxin in the sample solution contacts the adsorbent, thereby the endotoxin is adsorbed on the adsorbent. Usually, after adsorption of the endotoxin on the endotoxin adsorbent, washing is carried out with endotoxin-free water, buffer or the like to remove the non-adsorbed substances.

Alternatively, the above steps may be carried out as follows. The adsorbent and sample solution are contacted and, if necessary, washing is carried out to remove the non-adsorbed substances and then the adsorbent having an endotoxin adsorbed thereon is filled in the column as described above.

The step to react the detecting reagent with the endotoxin adsorbed on the endotoxin adsorbent can be carried out by discharging the adsorbent having the endotoxin adsorbed thereon from the tip opening into the detecting reagent or introducing the detecting reagent into the column through the tip opening by increasing the negative pressure and then reacting the endotoxin with the detecting reagent while the endotoxin is maintained on the adsorbent.

In case of introducing the endotoxin-detecting reagent into the column, the subsequent reaction and determination can be carried out (i) in the column by leaving the adsorbent packed in it, or (ii) in a container for incubation after discharging the adsorbent and the detecting reagent into the container through the tip opening of the column (by stopping application of negative pressure or inversely applying pressure through the rear end opening of the column).

As an endotoxin detecting reagent, known reagents, for example, a Limulus reagent (containing LAL, and a color developing substrate having chromophore or fluorophore), a labelled antibody against endotoxin or the like can be used under the known reaction conditions. For example, a Limulus reagent is incubated at 25° to 40° C., usually, at 37° C. for 10 to 120 minutes as disclosed in EP-A 456252 to complete the reaction. After the reaction is stopped, the measurement of absorbance, fluorescence or the like is carried out.

The step of determination can be carried out according to the known methods. For example, it can be carried out by measuring the absorbance or intensity of fluorescence by using measuring devices, and then determining the amounts by using calibration curve previously prepared. Or, it can be carried out by watching with eyes and comparing the extent of colouring with those of standard-samples which were treated in the same manner.

The apparatus for determination of the present invention comprises:

a column having a tip opening, a rear end opening and an adsorbent-filling and holding means provided in the column through which a sample solution can pass, at least one container having one opened end which can contain therein an adsorbent suspension, and a sample solution or a detecting reagent, the tip part of the column being able to be inserted into the container, a means for maintaining the column in the contained state in the container, and a negative pressure loading means communicated with a rear end of the column.

One embodiment of the apparatus of the present invention is shown in the schematic view of accompanying FIG. 1.

In the embodiment of the apparatus shown in FIG. 1, there is provided a column 4 having a tip opening 1, a rear end opening 2 and a glass wool filter 3 through which a sample solution can pass, while an adsorbent does not, as an adsorbent-filling and holding means through which a sample solution can pass. The column 4 is not limited to specified ones. Usually, a column having a small diameter such as inner diameter of 1 to 2.5 mm and length of 50 to 150 mm is preferable. In so far as the measurement by a Limulus reaction is not adversely influenced, any materials can be used for the column. Examples of the materials are glass, metal, synthetic resin and the like.

The apparatus is also provided with a container 5 having one opened end 5 which can contain therein an adsorbent suspension, a sample solution or a detecting reagent, the tip part of the column being able to be inserted into the container. The container may be made of glass, metal or synthetic resin. The container in FIG. 1 has a tube-like shape. Alternatively, the container may have the shape of a cuvette, cell or the like. The same container may be used for containing an adsorbent suspension, a sample solution or a detecting reagent, or for the above incubation. Alternatively, one set of a plurality of separate containers having the same or different shape may be provided for each contained sample or the like or each use.

Further, the apparatus is provided with a means 7 for maintaining the column 4 in the contained state in the container. In order to effectively fill the adsorbent in the column and introduce a sample solution and a detecting reagent in the column by the negative pressure, the means 7 is a lid body for closing tight a container opening 5, which has a hole 8 for air vent (a hole for supplying or exhausting air). The means maintains the column 4 in the contained state in the container by penetrating the column through the lid body. In FIG. 1, the means makes a fitting with the opening of the container 5 and the column extends therethrough. For example, the means is a plug made of silicone rubber and thereby the column 4 is maintained in the perpendicular direction in the container 6 with the tip opening 1 down.

The hole 8 for air vent is packed with glass wool for preventing contamination derived from the outer atmosphere.

The rear end opening 2 of the column 4 is communicated with the negative pressure loading means 11 via a connecting conduit 10. Thereby, the negative pressure can be loaded to the column to fill the adsorbent and introduce the sample solution and the detecting reagent in the column. In FIG. 1, the negative pressure loading means 11 is an injection cylinder. Alternatively, other negative pressure-generating sources such as a plunger, vacuum pump, tube pump and the like can be used. Any materials can be used for the connecting conduit 10, in so far as they give no adverse influences on endotoxin measurement. Specifically, glass, synthetic resin, metal and the like can be used for the connecting conduit.

The apparatus for determination of the present invention may be provided with a plurality of sets composed of the above column, the means for maintaining the column and the containers, whereby a plurality of samples can be measured simultaneously. Alternatively, cycles of filling of the adsorbent in the column, introduction of the sample solution and detecting reagent in the column, discharge of the adsorbent and detecting reagent from the column, and the measurement of the sample can be automated by using the known method such as computer controlling.

Then, an embodiment of the method for determination of the present invention using the apparatus for determination of the present invention shown in FIG. 1 is explained below.

An endotoxin adsorbent 12 is filled in the column 4 by the negative pressure such as suction force and the like. A sample solution is then introduced in the column 4 and an endotoxin in the sample is adsorbed on the adsorbent 12. This adsorption operation is carried out, for example, by introducing an aqueous sample solution in the column filled with the adsorbent and passing therethrough. The operation conditions can be appropriately selected depending upon the particular sample solutions. Usually, 3 to 100 mg of the adsorbent is used per 1 ml of an aqueous sample solution. The endotoxin is specifically and effectively adsorbed thereon at 4° to 40° C., pH 4 to 8, preferably, pH 5 to 7, and the ionic strength of not higher than 0.2. Under such the conditions, the endotoxin in an aqueous sample solution is approximately completely adsorbed on the adsorbent by passing the aqueous sample solution through the column at rate of not higher than about 2 ml/min. As the result, the endotoxin becomes concentrated on the adsorbent. The measurement sensitivity can be increased by increasing an amount of the sample solution.

Alternatively, a sample solution and an adsorbent are pre-mixed and stirred to come into the contact in a container such as a tube or the like as described above and then the adsorbent suspension may be filled in the column.

After adsorption operation, if necessary, the non-adsorbed substances are removed by washing with pyrogen-free water or buffer. An endotoxin detecting reagent is then introduced in the column to come into contact with the adsorbent. Further, the adsorbent and endotoxin detecting reagent are discharged in the container 6 to react under the appropriate conditions. The absorbance of the reaction solution is then measured to calculate the concentration of the endotoxin in the sample.

In the present invention, the measurement operations can be automated by suitably combining a commercially available automated distributing device, an incubator for a Limulus reaction, and a plate reader for reading the absorbance of the reaction solution. For example, a cylinder column having a suitable inner diameter is provided at a probe part of an automated distributing apparatus such as Model RSP5051 manufactured by Tecan (Japan) Co., Ltd. to obtain an apparatus of the present invention and thereby the operations of the above respective steps can be carried out automatically.

Contamination by the endotoxin derived from the outer atmosphere of the operation system can be prevented by carrying out the above operations in a clean bench. As the result, the measurement can be carried out at higher precision.

As explained in the preceding description, the method for determination using the apparatus of the present invention can determine an endotoxin much more simply in comparison with the prior method. In addition, operations of the present method can be automated as described above. Since approximately complete closed system can be formed by placing a measurement system including the above apparatuses in a clean bench, the method and apparatus of the present invention can prevent contamination by endotoxins derived from the outer atmosphere, thereby an endotoxin can be measured at higher precision.

The following Examples illustrate the present invention in detail but are not to be construed to limit the scope thereof.

EXAMPLE 1

Study of Calibration Curve

The calibration curve was studied using the apparatus for determination shown in FIG. 1 as follows.

Each 4 ml of aqueous endotoxin solution (concentration: 0.00125 and 0.0025 endotoxin unit (EU)/ml) was prepared by adding a predetermined amount of endotoxin (EC-5) to an endotoxin-free phosphate buffer (pH 6.0, $\mu$=0.08). A suspension of 120 mg of an endotoxin adsorbent (PYROSEP absorbent beads manufactured by TANABE SEIYAKU CO., LTD.) (suspended in 1 ml of endotoxin free water) was filled in a glass column (inner diameter: 1.68 mm, length: 130 mm) communicated to an injection cylinder for suction via a connecting conduit and 4 ml of the above solution of an endotoxin or phosphate buffer was passed by suction though the column filled with the adsorbent. Then, non-adsorbed substances were removed by washing the column with 1 ml of a 20 mM aqueous sodium chloride solution and a 0.2 ml of a Limulus reagent [a mixed solution of Limulus amebocyte lysate solution and color developing synthetic substrate solution, QCL-1000 (manufactured by BioWhisttaker, Inc.)] was introduced into the column. A mixture of the adsorbent and Limulus reagent was discharged into a tube, incubated at 37° C. for one hour and the reaction was stopped by addition of 0.1 ml of a 25% aqueous solution of acetic acid. The reaction mixture was centrifuged to remove the adsorbent, the supernatant was transferred to a 96 well microtiterplate and the absorbance was measured at 405 nm using a plate reader.

Figure 2:
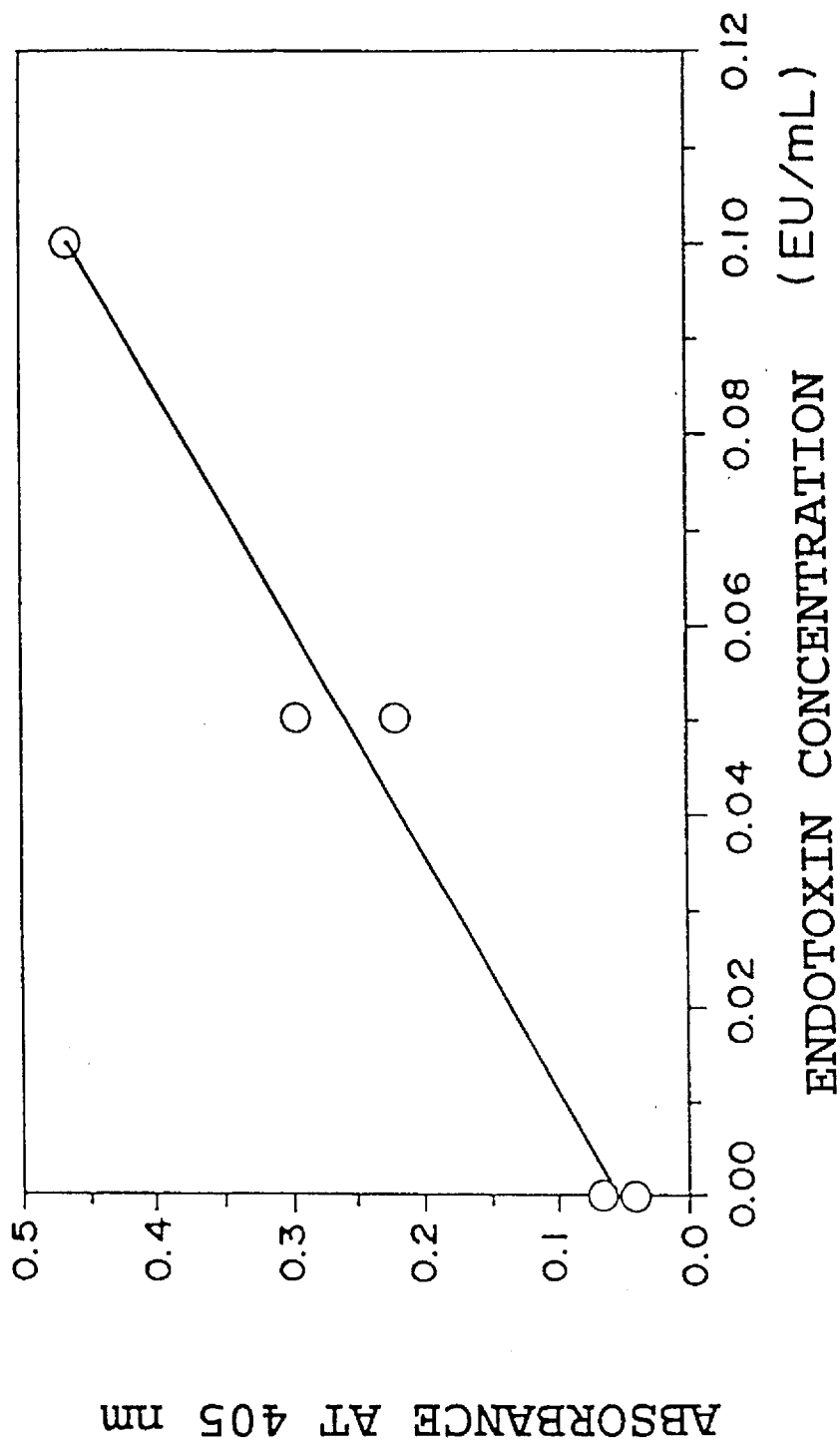
FIG. 2 is a graph showing the calibration curve obtained in Example 1.

When the data obtained were plotted on a graph wherein ordinates indicated the absorbance and abscissas indicated endotoxin concentration, the better calibration curve as shown in FIG. 2 was obtained.

EXAMPLE 2

Recovery of Endotoxin from Plasma

Endotoxin-free water (1.96 ml) and plasma (0.04 ml) were stirred to mix in a tube and the mixture was treated by heating in a boiling water bath for 10 minutes (control solution). Separately, 1.96 ml of endotoxin-free water and 0.04 ml of plasma containing endotoxin (EC-5, concentration: 0.1 EU/ml) were mixed and treated by heating as described above. These control solution and plasma solution containing endotoxin were processed according to the same manners as those in Example 1. An amount of the endotoxin adsorbed on the adsorbent was obtained using the calibration curve in FIG. 2 and the recovery rate was calculated. As the result, not less than 90% of the endotoxin added was found to be recovered.

EXAMPLE 3

Estimation of the Amount of the Endotoxin in Solution for Injection. Recovery of Endotoxin from Solution for Injection Aqueous solution of endotoxin was added into 30% Dextrose Injection by concentration of 0.5, 1.0 and 2.0 units of endotoxin/ml (EU/ml) to obtain the sample solutions. Into 4 ml of suspension of endotoxin adsorbent (endotoxin-free) [made by suspending 0.15 mg of PYROSEP absorbent beads into phosphate buffer solution (pH 6.0, $\mu=0.02$)] was added 0.04 ml of above-mentioned sample solution, and mixed.

Said suspension containing endotoxin was sucked into a glass column (inner diameter: 1.68 mm, length: 130 mm) which was communicated to an injection by a cylinder connecting conduit. Thus, the adsorbent in the suspension was filled in the column and then the filtrate was passed through. Next, said column was washed by sucking 1 ml of 20 mM NaCl solution to remove non-adsorbed substances. Limulus Reagent, [a mixed solution of Limulus Amebocyte Lysate solution and color developing synthetic substrate solution, QCL-1000 (manufactured by BioWhittaker, Inc.)] was introduced into each column. Said columns were incubated at 37° C. for 40 minutes.

Separately, standard solutions were made by adding endotoxin solution into endotoxin-free water to give concentration of 0.5, 1.0 and 2.0 EU/ml. Said standard solutions were treated as same manner as the sample solutions.

After the incubation, the extent of coloring of the sample were compared with those of the standard solutions. As the result, the coloring of standard solutions of different concentrations (0.5, 1.0, 2.0 EU/ml) were distinguishable from each other by sight, and the coloring of each sample solution showed almost same extent of coloring as that of corresponding standard solution. Accordingly, it was proved that the amount of endotoxin in the solution for injection could be determined generously by using this convenient and rapid method.

What is claimed is:

1. A method for determining an endotoxin by reacting the endotoxin adsorbed on an adsorbent having specific endotoxin adsorbability with an endotoxin detecting reagent, which comprises the steps of:
   (a) preparing a column having a tip opening, a rear end opening and an adsorbent-filling and holding means provided in the column through which a sample solution can pass,
   (b) introducing the endotoxin adsorbent into the column through the tip opening to fill and hold the adsorbent therein,
   (c) introducing the sample solution into the column through the tip opening and discharging the introduced sample solution through the rear end opening to contact the sample and the adsorbent and thereby adsorbing the endotoxin on the adsorbent,
   (d) reacting the detecting reagent with the endotoxin adsorbed on the adsorbent, and
   (e) detecting and determining the endotoxin wherein steps (b) and (c) are carried out by imposing a negative pressure at the rear end of the column.

2. The method for determining an endotoxin according to claim 1, wherein the adsorbent-filling and holding means is a filter provided in an intermediate part of the interior of the column or a rear end part of the column, through which a sample solution can pass, while the adsorbent does not.

3. The method for determining an endotoxin according to claim 1, wherein step (d) is carried out by introducing the detecting reagent in the column by loading of negative pressure through the rear end opening.

4. The method for determining an endotoxin according to claim 1, wherein a negative pressure is loaded by suction through the rear end opening of the column.

5. The method for determining an endotoxin according to claim 1, wherein step (e) is conducted by discharging the adsorbent and the detecting reagent from the column through the tip opening of the column and then incubating it.

6. The method for determining an endotoxin according to claim 5, wherein discharge is carried out by stopping application of a negative pressure or applying pressure through the rear end opening of the column.

7. The method for determining an endotoxin according to claim 5, wherein the column is maintained in a perpendicular direction with the tip down.

8. The method for determining an endotoxin according to claim 5, wherein the determination of an endotoxin is carried out after a predetermined amount of a sample solution is introduced in the column.

9. The method for determining an endotoxin according to claim 5, wherein the detecting reagent is a Limulus reagent.

10. The method for determining an endotoxin according to claim 5, wherein steps (b) and (c) are carried out in one step by introducing the endotoxin adsorbent and the sample solution in the column after contacting them.

11. The method for determining an endotoxin according to claim 1, wherein the determination of an endotoxin is carried out after a predetermined amount of a sample solution is introduced in the column.

12. The method for determining an endotoxin according to claim 1, wherein the detecting reagent is a Limulus reagent.

13. The method for determining an endotoxin according to claim 1, wherein the steps (b) and (c) are carried out in one step by introducing the endotoxin adsorbent and the sample solution in the column after contacting them.

* * * * *